US009343190B2

(12) United States Patent
Scheuren et al.

(10) Patent No.: US 9,343,190 B2
(45) Date of Patent: May 17, 2016

(54) APPARATUS FOR SCREENING OFF RADIATION DURING THE STERILIZATION OF CONTAINERS

(71) Applicant: KRONES AG, Neutraubling (DE)

(72) Inventors: Hans Scheuren, Bad Kreuznach (DE); Josef Knott, Schierling (DE); Michael Neubauer, Uebersee (DE)

(73) Assignee: KRONES AG (DE)

( * ) Notice: Subject to any disclaimer, the term of this patent is extended or adjusted under 35 U.S.C. 154(b) by 0 days.

(21) Appl. No.: 14/461,148

(22) Filed: Aug. 15, 2014

(65) Prior Publication Data

US 2015/0072041 A1   Mar. 12, 2015

(30) Foreign Application Priority Data

Sep. 10, 2013   (DE) ..................... 20 2013 104 114 U

(51) Int. Cl.
| | |
|---|---|
| *A61L 2/08* | (2006.01) |
| *B29C 49/42* | (2006.01) |
| *B65B 55/08* | (2006.01) |
| *G21F 3/04* | (2006.01) |
| *B29L 31/00* | (2006.01) |

(52) U.S. Cl.
CPC ... *G21F 3/04* (2013.01); *A61L 2/08* (2013.01); *A61L 2/082* (2013.01); *A61L 2/087* (2013.01); *B29C 49/421* (2013.01); *B29C 49/4273* (2013.01); *B65B 55/08* (2013.01); *A61L 2202/12* (2013.01); *A61L 2202/23* (2013.01); *B29L 2031/712* (2013.01)

(58) Field of Classification Search
CPC ........... A61L 2/08; A61L 2/082; A61L 2/087; A61L 2202/12; A61L 2202/23; B29C 49/4252; B29C 49/4273; B29C 49/68; B65B 55/08; G21F 3/04
See application file for complete search history.

(56) References Cited

U.S. PATENT DOCUMENTS

| | | | | |
|---|---|---|---|---|
| 2,336,443 | A | * | 12/1943 | West .............................. 220/476 |
| 4,025,294 | A | * | 5/1977 | Daane et al. ..................... 432/11 |
| 6,285,030 | B1 |  | 9/2001 | Williams et al. ......... 250/454.11 |

(Continued)

FOREIGN PATENT DOCUMENTS

| | | | |
|---|---|---|---|
| DE | 10 2010 012 569 | 9/2011 | ................ A61L 2/08 |
| EP | 1 144 983 | 11/2004 | ............. G01N 21/00 |

(Continued)

OTHER PUBLICATIONS

German Search Report issued in corresponding German Patent Appln. No. 20 2013 104 114.9 dated Jun. 20, 2014 (5 pgs).

(Continued)

*Primary Examiner* — Robert B Davis
(74) *Attorney, Agent, or Firm* — Hayes Soloway P.C.

(57) ABSTRACT

An apparatus for the sterilization of containers with a conveying device which conveys the containers along a predetermined conveying path (P), with a sterilization device which acts upon at least one area of the containers with charge carriers in the course of the sterilization, with a screening apparatus for screening off beams from the environment, which has at least two screening bodies which are arranged with respect to each other in such a way that one screening body is situated on the side of the screening apparatus facing the conveying path (P) and one screening body is situated on the one facing away from it, wherein the screening bodies are thermally insulated from each other.

29 Claims, 1 Drawing Sheet

(56) References Cited

U.S. PATENT DOCUMENTS

| | | | |
|---|---|---|---|
| 6,885,011 B2 | 4/2005 | Koenck et al. | 250/455.11 |
| 2010/0209290 A1 | 8/2010 | Cirri et al. | 422/22 |
| 2011/0012032 A1 | 1/2011 | Bufano et al. | 250/492.3 |
| 2011/0016829 A1* | 1/2011 | Drenguis et al. | 53/426 |
| 2012/0042611 A1* | 2/2012 | Lappe | 53/426 |
| 2012/0219455 A1* | 8/2012 | Meinzinger et al. | 422/22 |
| 2012/0248659 A1* | 10/2012 | Neubauer et al. | 264/523 |
| 2013/0015365 A1 | 1/2013 | Bufano et al. | 250/454.11 |
| 2013/0129566 A1* | 5/2013 | Knott et al. | 422/22 |
| 2014/0112826 A1 | 4/2014 | Knott et al. | 422/22 |
| 2014/0231673 A1 | 8/2014 | Yokobayashi et al. | 250/455.11 |
| 2014/0299786 A1 | 10/2014 | Yokobayashi et al. | 250/455.11 |
| 2014/0369885 A1 | 12/2014 | Krueger | 422/22 |

FOREIGN PATENT DOCUMENTS

| | | | |
|---|---|---|---|
| EP | 1982920 | 10/2008 | B65B 55/08 |
| EP | 2 371 397 | 10/2011 | A61L 2/08 |
| EP | 2594493 | 5/2013 | A61L 2/08 |
| EP | 2 724 731 | 4/2014 | A61L 2/08 |
| EP | 2 769 740 | 8/2014 | A61L 2/08 |
| EP | 2 769 922 | 8/2014 | A61L 2/08 |
| JP | 11-248892 | 9/1999 | G21K 5/00 |
| WO | WO 2008/129397 | 10/2008 | |
| WO | WO 2013/092735 | 6/2013 | A61L 2/08 |

OTHER PUBLICATIONS

Extended European Search Report issued in corresponding European appln., Feb. 5, 2015 (5 pgs).

Office Action issued in U.S. Appl. No. 14/274,478, dated Oct. 8, 2015 (39 pgs).

Extended European Search Report issued in corresponding European Patent Appln. No. 14001716.1-1356 dated Oct. 20, 2014 (6 pgs).

* cited by examiner

APPARATUS FOR SCREENING OFF RADIATION DURING THE STERILIZATION OF CONTAINERS

BACKGROUND OF THE INVENTION

The present invention relates to an apparatus for the sterilization of containers. It has long been known in the field of the beverage-producing industry to sterilize the containers to be filled, in particular before they are filled. To this end, chemical substances such as hydrogen peroxide or peracetic acid were generally used in the past. The drawback of this sterilization is that the chemical substances have to be rinsed out of the containers with sterile water after the respective treatment. In recent years, therefore, there has been a change to carrying out the sterilization of the containers by irradiation, and in particular by irradiation with electrons or charge carriers. In this case undesired radiation, and in particular x-ray radiation, occurs as an undesired side effect. The protection of the environment and, in particular, the operator of the plant from undesired radiation is therefore particularly important. For this purpose a screening is required which does not permit the escape of the types of radiation which occur.

In this case the present practice is for the screening off to be carried out in particular with high-density materials such as lead. On account of its toxicity, however, this material is undesired in the field of foodstuffs and therefore also in an associated packaging machine. In addition, lead is mechanically more vulnerable than other materials. Any damage to the material or simply time-dependent flowing leads to possible leaks and thus to the escape of radiation. In this context the removal of the lead also has to be taken into consideration when dismantling the machine.

Use is therefore also made of sufficiently thick screens of steel and castings with a high degree of mechanical stability and conformity to foodstuffs as a more advantageous screening. In this case too, an unchanged drawback, however, is that a considerable amount of energy is required in order to heat the thick plates. Such a heating is necessary for example before the beginning of the sterilization, since the surfaces of the sterilization plant have to be disinfected beforehand. This can be carried out for example by means of hydrogen peroxide gas at 70° C. In the case of screening plates which are sufficiently thick to ensure the protection of the operator of the plant, a heating requires a considerable amount of energy and long process times.

The object of the present invention is therefore to reduce the energy consumption and the process time in the case of heating at the same time as an extensive screening of radiation and with a high degree of security. In this case surfaces containing lead are to be avoided in the vicinity of packaging material and corrosion of the screening is to be minimized.

SUMMARY OF THE INVENTION

An apparatus according to the invention for the sterilization of containers has a conveying device which conveys the containers along a pre-set conveying path. Furthermore, the apparatus has at least one sterilization device which acts upon the containers with charge carriers for their sterilization during their conveying.

In addition, the apparatus has a screening apparatus which is used for screening off undesired radiation, and in particular radiation arising during the sterilization process and/or during the stressing of the plastics material containers with electron radiation. It is advantageous for the plastics material containers to be plastics material pre-forms.

This screening apparatus has in this case at least two screening bodies. These screening bodies are arranged with respect to each other in such a way that one screening body is situated on the side facing the conveying path and one screening body is situated on the one facing away from it. In this case the screening bodies are advantageously walls. These can preferably be arranged parallel to each other.

The screening bodies preferably extend in this case at least locally along the conveying path and/or laterally beside the conveying path of the containers. In this case, however, extending along the conveying path need not necessarily be understood as meaning that the screening bodies are curved in the same way as the conveying path. In this way, it would also be possible for example for a portion of the screening apparatus which extends along a straight portion to be used for the screening of a curved conveying path of the containers. It would also be possible in this case for the screening body facing the conveying path to be dispensed with at certain points along the conveying path if the radiation stressing at these points is so low that the screening body facing away from the conveying path can be produced with little material.

According to the invention the screening bodies are thermally insulated from each other. It is advantageous for this thermal insulation to be carried out with the aid of a gap which preferably extends at least locally between the screening bodies. This gap is preferably filled with a gaseous medium such as for example air. Other insulating materials, however, are also possible in this case. By means of this insulation a sandwich-like design is made possible by which—when the surface facing the conveying path is heated, as may be necessary for example during a sterilization of the sterilization plant—it is not necessary for the screening body of large mass facing away from the conveying path to be jointly heated but only the screening body facing the conveying path. In this way, the energy consumption and the process times can be reduced. The screening body facing the conveying path or the containers respectively is thus also used to separate the screening body facing away from the conveying path.

It is advantageous for the screening bodies to be joined to each other and they are preferably joined by welding seams, spot welds and/or screw connections or, in a particularly preferred manner, by plug-in connections. As a result, it is advantageous for the screening body facing the conveying path to have a pre-set movability as compared with the one facing away. This is preferably provided at a right angle to the conveying path and it permits, in particular, an extension of the screening body, which in particular is caused by thermal stressing.

It is preferable for the screening bodies to be arranged so as to be stationary with respect to each other, but it would also be possible for at least one, and preferably the screening body facing the containers, to be moved jointly with the containers.

The screening body which faces away from the conveying path is preferably a steel sheet or the face of a casting. In this case the thickness of the screening body is chosen in such a way that a reliable screening of the radiation takes place. To this end, it preferably has a thickness which is between 10 mm and 150 mm, preferably between 20 mm and 120 mm and in a particularly preferred manner between 28 mm and 102 mm. In this case the radiation to be screened off can be for example the ionizing radiation for the sterilization, i.e. in particular electron radiation, or interference radiation resulting from the sterilization, such as for example x-ray radiation.

The screening body which faces the conveying path is preferably a metal sheet which is resistant to sterilization media. This advantageously has a thickness of less than 10 mm, preferably of less than 5 mm and in a particularly preferred manner of less than 3 mm.

It is advantageous for the apparatus additionally to have a heating device for heating at least one screening body. The screening body to be heated is preferably the screening body facing the conveying path. The heating of the screening body is advantageously carried out in this case by the introduction of a heated gaseous medium. It would also be possible, however, for an electronic heating device to be used. Each screening means can therefore advantageously contain a heating element.

In this way, as a result of the thermal insulation according to the invention, only the screening body facing the conveying path is preferably heated, whereas the screening body of large mass facing away from the conveying path need not be heated.

For heating the surface of the screening body facing the conveying path, therefore, it is preferable for only the thermal energy to be necessary which is necessary for heating the screening body facing the conveying path.

In the case of a further advantageous embodiment the apparatus has a plurality of sterilization devices. It is preferable in this case for at least one sterilization device to be provided for the sterilization of at least one region of the inner wall of the containers. It is advantageous for the apparatus also to have an external stressing device for the sterilization of at least one portion of an outer wall of the containers. It is preferable for the apparatus for the external sterilization of the containers to be arranged so as to be stationary with respect to the movement of the containers.

In the case of a further advantageous embodiment the apparatus has an internal treatment device and this internal treatment device preferably has a radiation element, the longitudinal direction of which preferably extends substantially at a right angle to the conveying path of the containers and which is preferably capable of being introduced into the interior of the containers to be sterilized by a relative movement of the container with respect to the radiation element through an aperture in the containers to be sterilized. In addition, it is preferable for this internal treatment device to have an acceleration device for the acceleration of charge carriers, as well as an outlet window which is provided in such a way that it is capable of being inserted through an aperture of the containers into the latter. It is preferable for the charge carriers to be charged particles, and in particular electrons.

It is advantageous for the named outlet window to be a foil, and in particular a titanium foil. In this case this foil preferably has a thickness which is between 6 µm and 20 µm, preferably between 8 µm and 16 µm, and in a particularly preferred manner between 8 µm and 12 µm.

Furthermore, in the case of an advantageous embodiment the screening apparatus also has provided inside it sterilization devices by means of which a sterilization of parts of the screening apparatus and of parts of the plant such as for example of gripping clamps, conveying star wheels and the like can be carried out, so that a sterilization can be carried out in particular, but not exclusively, when the plant is started up again.

In addition, the conveying device preferably has a movable carrier on which are arranged a plurality of holding elements for holding the containers. The holding elements can be in particular, but not exclusively, gripping elements which can grip the containers in the pre-set portion, for example below the aperture thereof or below the carrying ring thereof respectively.

The present invention further relates to an apparatus for screening off radiation in an apparatus for the sterilization of containers, which has a conveying device, which conveys the containers along a pre-set conveying path, and a plurality of sterilization devices, the apparatus having at least two screening bodies which are arranged with respect to each other in such a way that one screening body is situated on the side of the apparatus facing the conveying path and one screening body is situated on the one facing away from it, and the screening body facing the conveying path can be heated. It is possible in this case for the screening effect of the two screening bodies to be clearly different (as in the case of the apparatus specified above) and, in particular, for the screening body facing the conveying path to have only a slight screening effect or (virtually) no screening effect in the case of x-ray radiation.

According to the invention the screening bodies are thermally insulated from each other. It is advantageous for this thermal insulation to be carried out with the aid of a gap which preferably extends at least locally between the screening bodies. This gap is preferably filled with a gaseous medium such as for example air.

In the case of an advantageous design the screening bodies are joined to each other. In this case it is advantageous for the screening bodies to be joined by welding seams, spot welds, screw connections or, in a particularly preferred manner, by plug-in connections. As a result, it is advantageous for the screening body facing the conveying path to be given a pre-set movability as compared with the one facing away. This is preferably provided at a right angle to the conveying path and/or at a right angle to a surface of the screening body, and it permits, in particular, an extension of the screening body, which in particular is caused by thermal stressing.

In this case the screening bodies are advantageously walls. These are preferably arranged parallel to each other.

It is preferable for the conveying path to extend between two screening bodies which face the conveying path (and preferably also between two screening bodies which face away from the conveying path) and it is preferable in this case for a duct, inside which the conveying path extends, to be formed by the aforesaid screening bodies.

The present invention further relates to an apparatus for the blow moulding of plastics material pre-forms or for the shaping of plastics material pre-forms into plastics material containers respectively. This apparatus has, in particular, a stressing device, such as a blow moulding nozzle, which acts upon the plastics material pre-forms with a medium, in particular compressed air, in order to shape the plastics material pre-forms into plastics material containers. In addition, it has a conveying device, which conveys the plastics material pre-forms along a pre-determined conveying path, and a wall apparatus, which has at least two walls which are arranged with respect to each other in such a way that one wall is situated on the side of the wall apparatus facing the conveying path and one wall is situated on the one facing away from it. According to the invention these walls are thermally insulated from each other. In this case the walls can preferably have the designs described above. It is preferable for the apparatus for the blow moulding additionally to have at least one sterilization device.

In the case of a further advantageous embodiment the apparatus for blow moulding also has a stretch rod which is capable of being inserted into the containers in order to stretch them in the longitudinal direction thereof. It is pointed out that the concept described here is also capable of being applied to other plants and machines for the treatment of containers, such as for example to filling devices.

BRIEF DESCRIPTION OF THE DRAWINGS

Further advantages and embodiments are evident from the accompanying drawings. In the drawings

DETAILED DESCRIPTION OF THE INVENTION

Figure 1:
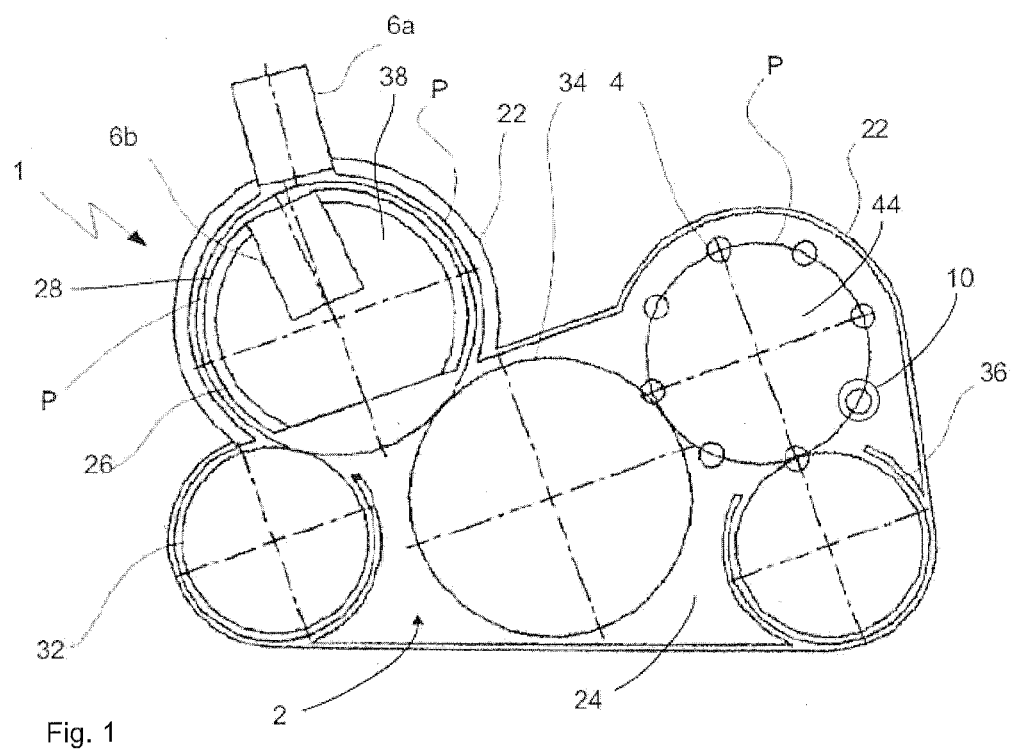
FIG. 1 is an illustration of an apparatus for the sterilization of containers.

FIG. 1 is an illustration of an apparatus 1 for the sterilization of containers 10. In this case the containers 10 are supplied to the apparatus 1 by way of a supply opening (not shown) and a supply device 32 which is designed in this case in the form of a supply star wheel. After that, an external sterilization of the containers 10 is carried out. The latter are conveyed in this case on a circular portion of a conveying path past two external sterilization devices 6a and 6b which irradiate an external surface of the containers with charge carriers, and in particular electrons. The reference number 38 designates in a roughly diagrammatic manner a conveying element such as a conveying star wheel, which is used for conveying the containers during the external sterilization thereof. This conveying element can have in this case a rotatable carrier on which are arranged a plurality of holding devices for holding the containers. The conveying path of the containers is bounded in this region both by the wall 22 towards the outside and by the wall 26 towards the inside.

After that, the containers are conveyed by a conveying element 34 to an internal treatment device. This conveying element 34 can be a conveying star wheel which also allows a distribution delay between the individual containers 10.

The reference number 4 refers to second sterilization devices which are arranged on a common and rotatable carrier 44. In this case these second sterilization devices 4 have rod-like bodies in each case, which are capable of being inserted into an interior of the containers in order to act upon the latter in this way with the charge carriers. In this case the lower ends of these rod-like bodies have in each case an outlet window through which the charge carriers can pass out of these rod-like bodies.

The reference number 36 designates a removal device which removes the sterilized containers 10 out of the apparatus 1 again. In this case this removal device 36 can also be designed in the form of a conveying star wheel. The reference number 2 refers to the conveying device in its entirety, which in this case has the individual conveying elements described above.

In order to screen off the x-ray radiation which occurs both during the external sterilization and during the internal sterilization, the apparatus has a screening apparatus 22 which in this case surrounds the entire conveying path P of the containers 10. The radiation is screened off at the top by a cover 28 and at the bottom by a base wall 24.

Figure 2:
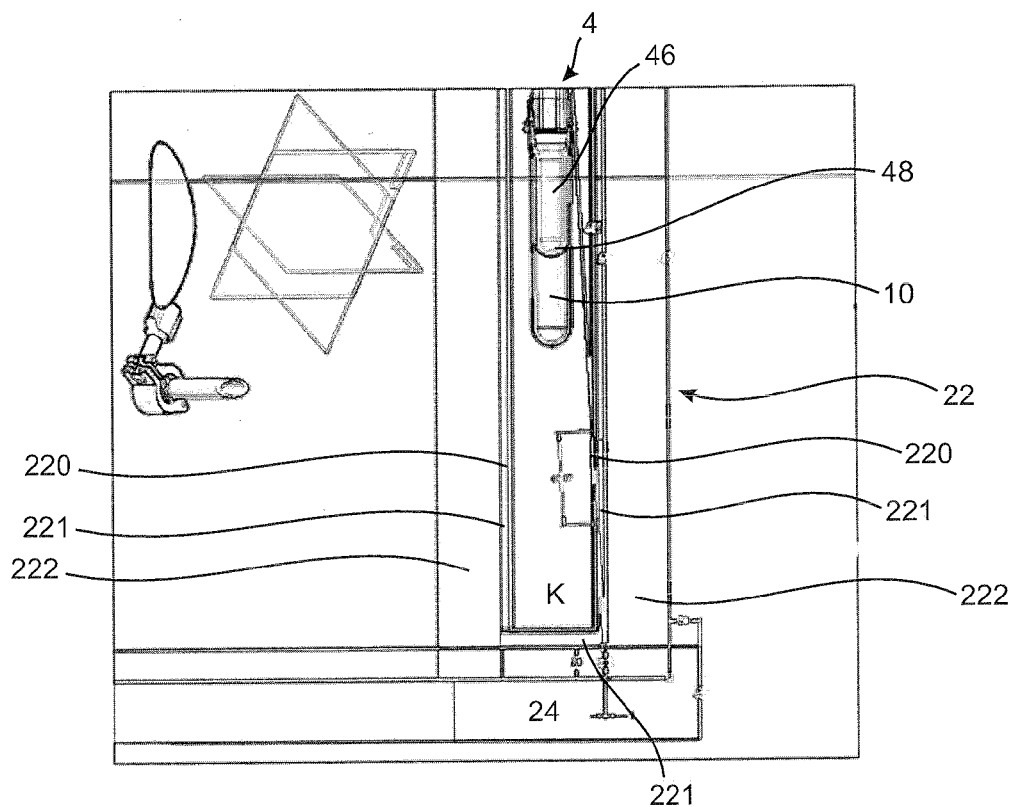
FIG. 2 is a detailed illustration of the screening apparatus.

FIG. 2 is a more detailed illustration of the screening apparatus 22. The screening apparatus 22 has in this case two screening bodies 220 and 222 in each case, the screening body 220 facing the conveying path of the containers 10 and the screening body 222 facing away from the conveying path. In this case the conveying path extends inside the channel K which is bounded by two screening bodies 220. The screening body 220 has in this case a smaller thickness than the screening body 222. As a result it is possible to reduce the time for heating the walls which are facing the conveying path of the plastics material pre-forms. In particular, the walls are heated to a temperature which is above 50° C., in a particularly preferred manner above 60° C. and preferably in a range of approximately 70° C. An insulating gap 221 will be noted between the screening bodies. It is possible, however, for the gap 221 to be replaced by a material for thermal insulation. In addition, the base wall 24 and the internal sterilization device 4 including the radiation element 46 are also formed with an outlet window 48.

The apparatus 1 according to the invention can have arranged downstream of it a shaping device (not shown) which shapes the plastics material pre-forms into the plastics material containers. This shaping device can have in this case a conveying device, such as for example a blow moulding wheel, on which are arranged a plurality of shaping stations. In addition, this shaping device can have arranged upstream of it a furnace which heats the plastics material pre-forms before the expansion thereof. The sterilization apparatus described here is advantageously situated between this furnace and the shaping device. In this way, it is preferable in this case for the already heated plastics material pre-forms to be sterilized and then expanded to form the plastics material containers. It is preferable for walls to be arranged around the sterilization apparatus, the walls being formed from screening bodies. In this case the screening body facing the sterilization apparatus is made thinner in its thickness than the screening body facing away from the sterilization apparatus. The screening bodies are arranged so as to be preferably thermally insulated from each other by an air gap.

The Applicants reserve the right to claim all the features disclosed in the application documents as being essential to the invention, insofar as they are novel either individually or in combination as compared with the prior art.

LIST OF REFERENCES

P conveying path
K channel
1 apparatus
2 conveying device
4 sterilization devices/internal sterilization device
6a sterilization device
6b sterilization device
10 containers
22 wall/screening apparatus
24 base wall
26 wall
28 cover
32 supply device
34 conveying element
38 conveying element
44 carrier
46 radiation element
48 outlet window
220 screening body
221 insulating gap
222 screening body

The invention claimed is:

1. An apparatus for the sterilization of containers comprising a conveying device which conveys the containers along a pre-determined conveying path (P), a plurality of sterilization devices which acts upon at least one area of the containers with charge carriers in the course of the sterilization, a screening apparatus for screening off beams from the environment, which has at least two screening bodies which are arranged with respect to each other in such a way that one screening body is situated on the side of the screening apparatus facing the conveying path (P) and one screening body is situated on the side of the screening apparatus facing away from the conveying path (P), wherein the screening bodies are thermally insulated from each other.

2. The apparatus according to claim 1, wherein the screening bodies are walls which extend along the conveying path (P).

3. The apparatus according to claim 1, wherein the screening bodies extend parallel to each other.

4. The apparatus according to claim 1, wherein the screening bodies are thermally insulated from each other via a gap which extends at least locally between the screening bodies.

5. The apparatus according to claim 4, wherein the gap between the screening bodies is filled with air.

6. The apparatus according to claim 1, wherein the screening bodies are joined to each other.

7. The apparatus according to claim 6, wherein the screening bodies are joined by welding seams, spot welds, screw connections or plug-in connections.

8. The apparatus according to claim 1, wherein the screening body facing the conveying path (P) has a pre-set movability at a right angle to the conveying path as compared with the screening body facing away from the conveying path.

9. The apparatus according to claim 1, wherein the screening body which faces away from the conveying path (P) is a steel sheet or the face of a casting.

10. The apparatus according to claim 1, wherein the screening body facing the conveying path (P) is a metal sheet which is resistant to sterilization media.

11. The apparatus according to claim 1, wherein the screening body facing away from the conveying path (P) is from 10 to 150 mm in thickness.

12. The apparatus according to claim 1, wherein the screening body facing the conveying path (P) is less than 10 mm in thickness.

13. The apparatus according to claim 1, wherein the screening bodies facing the containers are thinner than the screening bodies facing away from the containers.

14. The apparatus according to claim 1, wherein the radiation to be screened off is ionizing radiation for the sterilization of the containers or interference radiation resulting from the sterilization.

15. The apparatus according to claim 14, wherein the ionizing radiation comprises electron radiation.

16. The apparatus according to claim 14, wherein the interference radiation comprises x-ray radiation.

17. The apparatus according to claim 1, wherein a heating device is provided for heating at least one screening body.

18. The apparatus according to claim 17, wherein the screening body to be heated is the screening body facing the conveying path.

19. The apparatus according to claim 17, wherein the heating is carried out by the introduction of a heated gaseous medium.

20. The apparatus according to claim 1, wherein the sterilization device sterilizes at least one region of the inner wall of the containers.

21. The apparatus according to claim 20, wherein the sterilization device has a radiation element, the longitudinal direction of which extends substantially at a right angle to the conveying path (P) of the containers and which is capable of being introduced into the interior of the container to be sterilized by a relative movement of the container with respect to the radiation element through an aperture in the containers to be sterilized.

22. The apparatus according to claim 21, wherein the radiation element has an outlet window through which the sterilizing radiation can emerge.

23. The apparatus according to claim 21, wherein the outlet window is formed of a titanium foil.

24. The apparatus according to claim 1, wherein the conveying device has gripping elements.

25. An apparatus for the screening off of radiation in an apparatus for the sterilization of containers, comprising a conveying device, which conveys the containers along a pre-determined conveying path (P), and a plurality of sterilization devices, wherein the apparatus having at least two screening bodies which are arranged with respect to each other in such a way that one screening body is situated on the side of the apparatus facing the conveying path (P) and one screening body is situated on the side of the apparatus facing away from the conveying path (P), and the screening body facing the conveying path can be heated, and wherein the screening bodies are thermally insulated from each other.

26. The apparatus according to claim 25, wherein the screening bodies are joined to each other.

27. The apparatus according to claim 25, wherein the screening bodies are walls which extend along the conveying path (P).

28. An apparatus for the blow moulding of plastics material pre-forms comprising a conveying device, which conveys the plastics material pre-forms along a pre-determined conveying path (P), a stressing device, which acts upon the plastics material pre-forms with a medium in order to shape the plastics material pre-forms into plastics material containers, said apparatus comprising a plurality of sterilizing devices which act upon at least one area of the containers with charge carriers in the course of the sterilization and a wall apparatus, which has at least two walls which are arranged with respect to each other in such a way that one wall is situated on the side of the wall apparatus facing the conveying path (P) and one wall is situated on the one facing away from the conveying path (P), wherein the walls are thermally insulated from each other wherein the wall apparatus comprises a screening apparatus for screening off beams from the environment.

29. The apparatus according to claim 8, wherein the screening body facing the conveying path (P) is stretchable.

* * * * *